United States Patent [19]

Bashkirov et al.

[11] 4,056,572

[45] Nov. 1, 1977

[54] METHOD FOR THE MANUFACTURE OF PHENOLS

[76] Inventors: Andrei Nikolaevich Bashkirov, Novopeschanaya ulitsa, 21, korpus 1, kv. 13; Mark Markovich Grozhan, prospekt Kalinina, 31, kv. 49; Vladimir Vasilievich Kamzolkin, ulitsa Vavilova, 55/5, kv. 25; Jury Anatolievich Lapitsky, Leninsky prospekt, 83, korpus 2, kv. 226; Irina Vladimirovna Vygodskaya, ulitsa Novatorov, 36, korpus 9, kv. 38, all of Moscow, U.S.S.R.

[21] Appl. No.: 444,984

[22] Filed: Feb. 22, 1974

Related U.S. Application Data

[63] Continuation of Ser. No. 887,339, Dec. 22, 1969, abandoned.

[51] Int. Cl.$^2$ .................... C07C 39/06; C07C 39/08; C07C 67/05
[52] U.S. Cl. .................... 260/624 R; 260/621 G; 260/625; 560/131
[58] Field of Search ........... 260/621 G, 621 R, 624 R, 260/479 R, 625

[56] References Cited

U.S. PATENT DOCUMENTS

| 3,408,409 | 10/1968 | Coffey et al. | 260/621 G |
| 3,646,226 | 2/1972 | Smetana et al. | 260/621 G |
| 3,718,629 | 2/1973 | Heck | 260/621 G |

FOREIGN PATENT DOCUMENTS

| 1,029,419 | 5/1966 | United Kingdom | 260/621 G |
| 1,120,228 | 7/1968 | United Kingdom | 260/621 G |
| 176,915 | 2/1966 | U.S.S.R. | 260/621 G |

*Primary Examiner*—James O. Thomas, Jr.
*Assistant Examiner*—W. B. Lone
*Attorney, Agent, or Firm*—Haseltine, Lake & Waters

[57] ABSTRACT

A method for the production of phenols which comprises subjecting alkylaromatic hydrocarbons to liquid-phase oxidation with oxygen at a temperature of 100°-300° C and under a pressure of 1-100 atm in the presence of an acidic catalyst taken in an amount of 0.0006-10 mole % and also in the presence of carboxylic acid anhydrides or chlorides, followed by saponifying the resulting phenolic esters.

14 Claims, No Drawings

METHOD FOR THE MANUFACTURE OF PHENOLS

This application is a continuation of Ser. No. 887,339, filed Dec. 22, 1969, now abandoned.

This invention relates to methods for the production of phenols.

Phenols find application for manufacturing phenolic resins, synthetic polyamide fibers, epoxy resins derived from bisphenol A, lubricating oil additives, herbicides, etc.

Among various known processes of producing phenols, the chlorination and sulfonation methods, the cumene process and also the preparation of phenol by toluene oxidation are more extensively used.

The cumene process consists in that cumene prepared by alkylating benzene with propylene is subjected to liquid-phase oxidation with atmospheric oxygen at a temperature of 70°–90° C to cumene hydroperoxide, the degree of oxidation being 20–30%, followed by cleaving the hydroperoxide to phenol and acetone.

The cumene process, despite its extensive use, suffers from a number of disadvantages, such as:

1. The necessity of employing pure benzene which is a scarce raw material;
2. The process involves two stages;
3. A relatively low process efficiency, and
4. Explosion hazards.

The process of producing phenol by toluene oxidation to benzoic acid and subsequent decarboxylation of the benzoic acid formed also involves two stages and, moreover, does not make it possible to obtain the desired product in good yield. When used for the manufacture of cresols from xylene, this method yields a mixture of isomers and is, therefore, disadvantageous.

The method of producing dihydric phenols by the oxidation of diisopropylbenzenes has not found extensive application because of the explosive nature of dihydroperoxides. Another disadvantage of the method is the formation of a substantial quantity of by-products, e.g. monohydroperoxides, hydroxyhydroperoxides, diols, etc.

It is an object of the present invention to eliminate the afore-mentioned disadvantages.

It is a further and more specific object of the invention to provide a method for the oxidation of alkylaromatic hydrocarbons which will make it possible to obtain in good yield mono- and polyhydric phenols of diverse structure and high purity, and also to extend the range of raw materials suitable for the preparation of said phenols.

This object is accomplished by the provision of a method for the production of phenols by the liquid-phase oxidation of alkylaromatic hydrocarbons by oxygen at elevated temperatures and pressure, wherein, according to the present invention, the process of oxidation is carried out at a temperature of 100°–300° C and under a pressure of 1–100 atm in the presence of an acidic catalyst taken to the extent of 0.0006–10 mole % and also in the presence of carboxylic acid anhydrides or chlorides, followed by the saponification of the esters formed from the phenols thus obtained.

The mechanism of the present process is as follows.

An alkylaromatic hydrocarbon reacts with oxygen and forms a hydroperoxide which, under the effect of an acidic catalyst, undergoes rearrangement to yield a phenol and an aliphatic aldehyde or ketone. An esterifying agent (carboxylic acid anhydride or chloride) reacts with the phenol formed and yields an ester, which is less susceptible to further oxidation than the phenol, the ester formation being also advantageous in that process inhibition due to the presence of phenol is eliminated because of marked diminution of the phenol concentration. The oxidation process having been completed, the aforesaid ester is saponified to yield the desired phenol.

To obtain polyhydric phenols, the esters of phenols containing alkyl groups in the ring are subjected, prior to the step of ester saponification, to liquid-phase oxidation with oxygen at a temperature of 100°–300° C and under a pressure of 1–100 atm in the presence of an acidic catalyst taken in an amount of 0.0006 to 10 mole % and also in the presence of organic acid anhydrides or chlorides.

The present invention of producing phenol is accomplished in the following manner.

Into a stainless steel reactor are charged an alkylaromatic hydrocarbon to be oxidized (e.g. toluene, xylene, ethylbenzene, cumene, or mesitylene), an esterifying agent (e.g. acetic anhydride, acetyl chloride, or propionic anhydride), and a catalyst (e.g. Lewis acids, sulfonic acids, strong mineral acids, or bisulfates). The reaction mixture is heated under pressure until the preset temperature is attained, the temperature, pressure and catalyst amount being selected depending upon the boiling point of the starting alkylaromatic hydrocarbon, as well as upon its oxidizability. Next air or a nitrogen-oxygen mixture (2.5–21 vol% of oxygen and 97.5–79 vol. % of nitrogen) is passed through the reactor for a prescribed period of time, followed by cooling the reactor, and rectifying the oxidate. The unconverted hydrocarbon and the esterifying agent are recycled back, while the phenolic esters are subjected to saponification to obtain the desired phenol, and the by-product aromatic aldehyde, aromatic ketone, aliphatic acid and the aromatic ester derived therefrom, together with the resinous reaction products, are withdrawn from the cycle.

To obtain polyhydric phenols, phenolic esters containing alkyl groups in the ring, for example p-cresolic, m-cresolic, o-cresolic, 3,5-xylenolic or 2,4-xylenolic esters, are subjected, prior to the saponification step, to oxidation in accordance with the procedure disclosed hereinbefore.

For a better understanding of the present invention, the following examples of the preparation of phenols are given by way of illustration.

EXAMPLE 1

Into a reactor are charged 850 g of toluene, 300 g of acetic anhydride, and 1 g of concentrated sulfuric acid as catalyst. Oxidation of the starting hydrocarbon is effected at a temperature of 220° C and under a pressure of 30 atm. by feeding into the reactor a nitrogen-oxygen mixture (oxygen content, 10% by volume) at a rate of 600 l/hr, toluene conversion after a 10–12 min. oxidation period being as high as 10%.

Under the conditions specified hereinabove, the oxidation of 100 g of toluene yields the following products, grams:

Phenol (after saponification of phenyl acetate by boiling in water) . . . 55 (56% of the theoretical
Cresols (after saponification of cresyl acetates ... 8
Benzaldehyde ... 14
Benzyl acetate ... 34.

EXAMPLE 2

Into a reactor are charged 850 g of ethylbenzene, 300 g of acetic anhydride, and 1 g of toluenesulfonic acid as catalyst. Oxidation of the starting hydrocarbon is effected at a temperature of 200° C and under a pressure of 20 atm by feeding into the reactor a nitrogen-air mixture as disclosed in Example 1. After 10–12 minutes, ethylbenzene is converted to the extent of 10%.

Under the conditions specified hereinabove, the oxidation of 100 g of ethylbenzene yields the following products, grams:

Phenol (after saponification of phenyl acetate) ... 50
 (56% of the theoretical)
Acetophenone ... 18
Benzaldehyde ... 10
α- Phenylethyl acetate ... 7.

EXAMPLE 3

Into a reactor are charged 850 g of o-xylene, 300 g of acetyl chloride, and 2 g of $ZnCl_2$ as catalyst. Oxidation of the starting hydrocarbon is conducted at a temperature of 180° C and under a pressure of 20 atm. by feeding into the reactor a nitrogen-oxygen mixture (oxygen content, 5% by volume) at a rate of 600 l/hr. After 25 minutes, the degree of o-xylene oxidation (conversion) is as high as 10%.

Under the conditions specified hereinabove, the oxidation of 100 g of o-xylene yields the following products, grams:

o-Cresol (after saponification of o-tolyl acetate) ... 36
 (37% of the theoretical)
Xylenols (after saponification of dimethylphenyl acetates) ... 2
o-Toluic aldehyde ... 27
o-Methylbenzyl acetate ... 38.

EXAMPLE 4

Into a reactor are charged 850 g of m-xylene, 500 g of propionic anhydride, and 2 g of $AlCl_3$ as catalyst. Oxidation of the starting hydrocarbon is conducted at a temperature of 200° C and under a pressure of 25 atm. by feeding into the reactor air (oxygen content, 21% by volume) at a rate of 600 l/hr. Within 5–6 minutes, the m-xylene is converted to the extent of 10%.

Under the conditions specified hereinabove, the oxidation of 100 g of m-xylene yields the following products, grams:

m-Cresol (after saponification of m-Tolyl propionate) . . . 20 (20% of the theoretical)
Xylenols (after saponification of dimethylphenyl propionates) ... 3.6
m-Methylbenzyl propionate ... 77
m-Toluic aldehyde ... 15.

EXAMPLE 5

Into a reactor are charged 850 g of p-xylene, 300 g of acetic anhydride, and 2.5 g of $NaHSO_4$ as catalyst. Oxidation of the starting hydrocarbon is carried out at a temperature of 200° C and under a pressure of 25 atm by feeding into the reactor a nitrogen-air mixture as described in Example 1. Within 10–12 minutes, the p-xylene is converted to the extent of 10%.

Under the conditions specified hereinabove, the oxidation of 100 g of p-xylene yields the following products, grams:

p-Cresol (after saponification of p-tolyl acetate) ... 50
 (50% of the theoretical)
2,5-Xylenol (after saponification of 1,5-dimethylphenyl acetate) ... 5
p-Toluic aldehyde ... 17
p-Methylbenzyl acetate ... 39.

EXAMPLE 6

Into a reactor are charged 1,000 g of p-xylene, 100 g of acetic anhydride, and 2 g of concentrated sulfuric acid as catalyst. Oxidation of the starting hydrocarbon is carried out at a temperature of 200° C and under a pressure of 25 atm. by feeding into the reactor a nitrogen-air mixture (oxygen content, 5% by volume) at a rate of 600 l/hr. Within 25 minutes, the p-xylene undergoes conversion to the extent of 10%.

Under the conditions specified hereinabove, the oxidation of 100 g of p-xylene yields the following products, grams:

p-Cresol (after saponification of p-tolyl acetate) ... 76
 (75% of the theoretical)
2,5-Xylenol (after saponification of 2,5-dimethylphenyl acetate) ... 4
p-Toluic aldehyde ... 6.5
p-Methylbenzyl acetate ... 11.

EXAMPLE 7

The reactants and oxidation procedure are identical to those disclosed in Example 6.

100 g of the p-tolyl acetate obtained, 30 g of acetic anhydride, and 0.18 g of concentrated sulfuric acid are placed in the reactor, and ester oxidation is conducted at 230° C and under a pressure of 20 atm. by feeding into the reactor a nitrogen-oxygen mixture (oxygen content, 10% by volume) at a rate of 60 l/hr. Within 10–12 minutes the ester undergoes conversion to the extent of 10%.

Under the aforespecified conditions, the oxidation of 10 g of p-tolyl acetate yields, on saponifying the resultant diacetate, 1.9 g of hydroquinone. The yield equals 20% of the theoretical amount.

EXAMPLE 8

Into a reactor are charged 850 g of mesitylene, 300 g of acetic anhydride, and 1.5 g of concentrated sulfuric acid as catalyst. Oxidation of the starting hydrocarbon is carried out at a temperature of 200° C and under a pressure of 15 atm by feeding into the reactor the nitrogen-oxygen mixture as disclosed in Example 1.

Within 10–12 minutes, the degree of mesitylene conversion equals 10%.

Under the conditions specified hereinabove, the oxidation of 100 g of mesitylene yields the following products, grams:

3,5-Xylenol (after saponification of 3,5-dimethylphenyl acetate) . . . 67 (67% of the theoretical)
3,5-Dimethylbenzyl acetate . . . 8
Mesitylenic aldehyde . . . 8.

EXAMPLE 9

Into a reactor are charged 850 g of p-xylene, 300 g of acetic anhydride, and 3 g of benzenesulfonic acid as catalyst.

Oxidation of the starting hydrocarbon is carried out at 250° C and under a pressure of 30 atm. by feeding into the reactor air as disclosed in Example 5.

Under the conditions specified hereinabove, the oxidation of 100 g of p-xylene yields the following products, grams:

p-Cresol (after saponification of p-Tolyl acetate) . . . 10 (10% of the theoretical)
2,5-Xylenol (after saponification of 2,5-dimethylphenyl acetate) . . . 2
p-Toluic aldehyde . . . 18
p-Methylbenzyl acetate . . . 75.

What is claimed is:

1. A method for the production of a monohydric phenol comprising subjecting an alkyl benzene wherein the alkyl moiety consists of at least one alkyl group selected from the group consisting of methyl and ethyl groups to liquid-phase oxidation with oxygen at a temperature of 180°–250° and under a pressure of 15–30 atm in the presence of
    a. 0.0006 to 10 mole percent of a strongly acidic catalyst and
    b. an esterifying agent selected from the group consisting of lower alkanoic carboxylic acid anhydrides and acid chlorides, followed by saponification or hydrolysis of the resulting monohydric phenolic ester to form the monhydric phenol.

2. A method according to claim 1 wherein the acidic catalyst is a Lewis acid.

3. A method according to claim 1 wherein the acidic catalyst is an acidic salt of a bivalent strong acid.

4. The method according to claim 1 wherein the acidic catalyst is sulfuric acid.

5. The method according to claim 1 wherein the acidic catalyst is p-toluenesulfonic acid.

6. The method according to claim 1 wherein the esterifying agent is acetic anhydride.

7. The method according to claim 1 wherein the esterifying agent is propionic anhydride.

8. The method according to claim 1 wherein the esterifying agent is acetyl chloride.

9. The method according to claim 2 wherein the Lewis acid is zinc chloride.

10. The method according to claim 2 wherein the Lewis acid is aluminum chloride.

11. The method according to claim 3 wherein the acidic salt of a bivalent strong acid is sodium bisulfate (NaHSO$_4$).

12. The method according to claim 1 wherein the alkyl benzene is selected from the group consisting of toluene, xylene, ethylbenzene and mesitylene.

13. A method for the production of a polyhydric phenol comprising subjecting a phenolic alkyl ester containing an alkyl group selected from the group consisting of methyl and ethyl groups in the aromatic ring to liquid-phase oxidation with oxygen at a temperature of 180°–250° C. and under a pressure of 15–30 atm in the presence of
    a. 0.0006 to 10 mole percent of a strongly acid catalyst and
    b. an esterifying agent selected from the group consisting of lower alkanoic carboxylic acid anhydrides and acid chlorides, followed by saponification or hydrolysis of the resulting polyhydric phenolic ester to from the polyhydric phenol.

14. A method of oxidizing an organic compound selected from the group consisting of toluene, xylene, ethyl benzene and trimethylbenzene to form a phenolic alkyl ester comprising subjecting said compound to liquid-phase oxidation with oxygen at a temperature of 180°–250° C. and under a pressure of 15–30 atm. in the presence of
    a. 0.0006 to 10 mole percent of a strongly acidic catalyst and
    b. an esterifying agent selected from the group consisting of lower alkanoic carboxylic acid anhydrides and acid chlorides.

* * * * *